United States Patent
Qi et al.

(10) Patent No.: US 11,447,783 B2
(45) Date of Patent: Sep. 20, 2022

(54) REDUCTION IN ACETATE PRODUCTION BY YEAST OVER-EXPRESSING PAB1

(71) Applicant: DANISCO US INC., Palo Alto, CA (US)

(72) Inventors: Min Qi, Hockessin, DE (US); Paula Johanna Maria Teunissen, Palo Alto, CA (US); Quinn Qun Zhu, West Chester, PA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 16/978,874

(22) PCT Filed: Mar. 4, 2019

(86) PCT No.: PCT/US2019/020526
§ 371 (c)(1),
(2) Date: Sep. 8, 2020

(87) PCT Pub. No.: WO2019/173204
PCT Pub. Date: Sep. 12, 2019

(65) Prior Publication Data
US 2020/0407734 A1   Dec. 31, 2020

Related U.S. Application Data

(60) Provisional application No. 62/639,183, filed on Mar. 6, 2018.

(51) Int. Cl.
| | | |
|---|---|---|
| *C12N 15/81* | (2006.01) | |
| *C12N 15/67* | (2006.01) | |
| *C12P 7/06* | (2006.01) | |
| *C12P 7/56* | (2006.01) | |

(52) U.S. Cl.
CPC ............. *C12N 15/81* (2013.01); *C12P 7/06* (2013.01); *C12P 7/56* (2013.01)

(58) Field of Classification Search
CPC .............. C12P 7/06; C12P 7/56; C12N 15/81
See application file for complete search history.

(56) References Cited

U.S. PATENT DOCUMENTS

| | | |
|---|---|---|
| 5,985,575 A | 11/1999 | Wickens et al. |
| 8,795,998 B2 | 8/2014 | Pronk et al. |
| 8,956,851 B2 | 2/2015 | Argyros et al. |
| 9,175,270 B2 | 11/2015 | Nevoigt et al. |
| 2012/0276587 A1 | 11/2012 | Beck et al. |
| 2013/0244243 A1* | 9/2013 | Matsuyama ........... C12N 15/81 435/6.13 |
| 2014/0273144 A1 | 9/2014 | Hawkins et al. |

FOREIGN PATENT DOCUMENTS

| | | |
|---|---|---|
| WO | 2015023989 A1 | 2/2015 |
| WO | 2015065871 A1 | 5/2015 |
| WO | 2015148272 A1 | 10/2015 |
| WO | 2017189421 A1 | 11/2017 |

OTHER PUBLICATIONS

Sonderreger et al., Applied and Environmental Microbiology, 70(5), 2892-2897, 2004.*
Altschul et al., "Basic Local Alignment Search Tool", J. Mol. Bio., 215, Nov. 1990, pp. 403-410.
Altschul et al., "Local alignment statistics", Methods in Enzymology, vol. 266, 1996, pp. 460-480.
Brune et al., "Yeast poly(A)-binding protein Pab1 shuttles between the nucleus and the cytoplasm and functions in mRNA export", RNA, vol. 11, 2005, pp. 517-531.
Devereux et al., "A comprehensive set of sequence analysis programs for the VAX", Nucleic Acids Research, vol. 12, No. 1, 1984, pp. 387-395.
Duskova et al., "Two glycerol uptake systems contribute to the high osmotolerance of Zygosaccharomyces rouxii", Molecular Microbiology vol. 97, No. 3, 2015, pp. 541-559.2015.
Feng et al., "Progressive sequence alignment as a prerequisite to correct phylogenetic trees", Journal of Molecular Evolution, J Mol Evol , 25, 1987, pp. 351-360.
Ferreira et al. "A Member of the Sugar Transporter Family, Stl1p Is the Glycerol/H+ Symporter in *Saccharaomyces cerevisiae*", Molecular Biology of the Cell, vol. 16, Apr. 2005, pp. 2068-2076.
Gombert et al., "Improving conversion yield of fermentable sugars into fuel ethanol in 1st generation yeast-based production processes", Current Opinion in Biotechnology, vol. 33, Jun. 2015, pp. 81-86.
Henikoff et al., "Amino acid substitution matrices from protein blocks", Proc. Natl. Acad. Sci. USA, vol. 89, Nov. 1992, pp. 10915-10919.
Higgins et al., "Fast and sensitive multiple sequence alignments on a microcomputer", Bioinformatics, vol. 5, Issue 2, Apr. 1989, pp. 151-153.
Karlin et al., "Applications and statistics for multiple high-scoring segments in molecular sequences", Proc. Natl. Acad. Sci. USA, vol. 90, Jun. 1993, pp. 5873-5877.
Martani et al., "The *Saccharomyces cerevisiae* poly(A) binding protein Pab1 as a target for eliciting stress tolerant phenotypes", Nature Scientific Reports, 5:18318, Dec. 14, 2015, pp. 1-13.
Needleman et al., "A General Method Applicable to the Search for Similarities in the Amino Acid Sequence of Two Proteins", J. Mol. Biol., 48, 1970, pp. 443-453.
Pearson et al., "Improved tools for biological sequence comparison", Proc. Natl. Acad. Sci. USA, vol. 85, Apr. 1988, pp. 2444-2448.
Smith et al., "Comparison of Biosequences", Advances in Applied Mathmatics 2, 1981, pp. 482-489.

(Continued)

*Primary Examiner* — Maryam Monshipouri

(57) ABSTRACT

Described are compositions and methods relating to modified yeast that over-express polyadenylate-binding protein (PAB1). The yeast produces a deceased amount of acetate compared to parental cells. Such yeast is particularly useful for large-scale ethanol production from starch substrates where acetate in an undesirable end product.

15 Claims, No Drawings

Specification includes a Sequence Listing.

(56) References Cited

OTHER PUBLICATIONS

Sonderegger et al., "Metabolic 1-11 Engineering of a Phosphoketolase Pathway for Pentose Catabolism in *Saccharomyces cerevisiae*", Applied and Environmental Microbiology, vol. 70, No. 5, May 1, 2004.

Swisher et al., "Localization to, 1-11 and Effects of Pbpl, Pbp4, Lsml2, Dhhl, and Pabl on Stress Granules in *Saccharomyces cerevisiae*", Plus One, vol. 5, No. 4, Apr. 2, 2010, 14 pages.

Thompson et al. "Clustal W" improving the sensitivity of progressive multiple sequence alignment through sequence weighting, position-specific gap penalties and weight matrix choice, Nucleic Acids Research, vol. 22, No. 22, 1994, pp. 4673-4680.

Wang et al., "RNA-Seq: a revolutionary tool for transcriptomics", Nat Rev Genet 10(1), Jan. 2009, pp. 57-63.

Zhang et al., "Engineering of the glycerol decomposition pathway and cofactor regulation in an industrial yeast improves ethanol production", J Ind Microbiol Biotechnol, 40, 2013, pp. 1153-1160.

\* cited by examiner

SEQUENCE LISTING

```
<160> NUMBER OF SEQ ID NOS: 4

<210> SEQ ID NO 1
<211> LENGTH: 577
<212> TYPE: PRT
<213> ORGANISM: Saccharomyces cerevisiae

<400> SEQUENCE: 1

Met Ala Asp Ile Thr Asp Lys Thr Ala Glu Gln Leu Glu Asn Leu Asn
1               5                   10                  15

Ile Gln Asp Asp Gln Lys Gln Ala Ala Thr Gly Ser Glu Ser Gln Ser
                20                  25                  30

Val Glu Asn Ser Ser Ala Ser Leu Tyr Val Gly Asp Leu Glu Pro Ser
            35                  40                  45

Val Ser Glu Ala His Leu Tyr Asp Ile Phe Ser Pro Ile Gly Ser Val
        50                  55                  60

Ser Ser Ile Arg Val Cys Arg Asp Ala Ile Thr Lys Thr Ser Leu Gly
65                  70                  75                  80

Tyr Ala Tyr Val Asn Phe Asn Asp His Glu Ala Gly Arg Lys Ala Ile
                85                  90                  95

Glu Gln Leu Asn Tyr Thr Pro Ile Lys Gly Arg Leu Cys Arg Ile Met
                100                 105                 110

Trp Ser Gln Arg Asp Pro Ser Leu Arg Lys Lys Gly Ser Gly Asn Ile
            115                 120                 125

Phe Ile Lys Asn Leu His Pro Asp Ile Asp Asn Lys Ala Leu Tyr Asp
130                 135                 140

Thr Phe Ser Val Phe Gly Asp Ile Leu Ser Ser Lys Ile Ala Thr Asp
145                 150                 155                 160

Glu Asn Gly Lys Ser Lys Gly Phe Gly Phe Val His Phe Glu Glu Glu
                165                 170                 175

Gly Ala Ala Lys Glu Ala Ile Asp Ala Leu Asn Gly Met Leu Leu Asn
            180                 185                 190

Gly Gln Glu Ile Tyr Val Ala Pro His Leu Ser Arg Lys Glu Arg Asp
        195                 200                 205
```

Ser Gln Leu Glu Glu Thr Lys Ala His Tyr Thr Asn Leu Tyr Val Lys
210                 215                 220

Asn Ile Asn Ser Glu Thr Thr Asp Glu Gln Phe Gln Glu Leu Phe Ala
225                 230                 235                 240

Lys Phe Gly Pro Ile Val Ser Ala Ser Leu Glu Lys Asp Ala Asp Gly
                245                 250                 255

Lys Leu Lys Gly Phe Gly Phe Val Asn Tyr Glu Lys His Glu Asp Ala
                260                 265                 270

Val Lys Ala Val Glu Ala Leu Asn Asp Ser Glu Leu Asn Gly Glu Lys
            275                 280                 285

Leu Tyr Val Gly Arg Ala Gln Lys Lys Asn Glu Arg Met His Val Leu
290                 295                 300

Lys Lys Gln Tyr Glu Ala Tyr Arg Leu Glu Lys Met Ala Lys Tyr Gln
305                 310                 315                 320

Gly Val Asn Leu Phe Val Lys Asn Leu Asp Asp Ser Val Asp Asp Glu
                325                 330                 335

Lys Leu Glu Glu Glu Phe Ala Pro Tyr Gly Thr Ile Thr Ser Ala Lys
                340                 345                 350

Val Met Arg Thr Glu Asn Gly Lys Ser Lys Gly Phe Gly Phe Val Cys
            355                 360                 365

Phe Ser Thr Pro Glu Glu Ala Thr Lys Ala Ile Thr Glu Lys Asn Gln
370                 375                 380

Gln Ile Val Ala Gly Lys Pro Leu Tyr Val Ala Ile Ala Gln Arg Lys
385                 390                 395                 400

Asp Val Arg Arg Ser Gln Leu Ala Gln Gln Ile Gln Ala Arg Asn Gln
                405                 410                 415

Met Arg Tyr Gln Gln Ala Thr Ala Ala Ala Ala Ala Ala Ala Ala Gly
                420                 425                 430

Met Pro Gly Gln Phe Met Pro Met Phe Tyr Gly Val Met Pro Pro
            435                 440                 445

Arg Gly Val Pro Phe Asn Gly Pro Asn Pro Gln Gln Met Asn Pro Met
            450                 455                 460

Gly Gly Met Pro Lys Asn Gly Met Pro Pro Gln Phe Arg Asn Gly Pro
465                 470                 475                 480

Val Tyr Gly Val Pro Pro Gln Gly Gly Phe Pro Arg Asn Ala Asn Asp
                485                 490                 495

Asn Asn Gln Phe Tyr Gln Gln Lys Gln Arg Gln Ala Leu Gly Glu Gln
                500                 505                 510

Leu Tyr Lys Lys Val Ser Ala Lys Thr Ser Asn Glu Glu Ala Ala Gly
            515                 520                 525

Lys Ile Thr Gly Met Ile Leu Asp Leu Pro Pro Gln Glu Val Phe Pro
530                 535                 540

Leu Leu Glu Ser Asp Glu Leu Phe Glu Gln His Tyr Lys Glu Ala Ser
545                 550                 555                 560

Ala Ala Tyr Glu Ser Phe Lys Lys Glu Gln Glu Gln Gln Thr Glu Gln
                565                 570                 575

Ala

<210> SEQ ID NO 2
<211> LENGTH: 1734
<212> TYPE: DNA
<213> ORGANISM: Artificial Sequence
<220> FEATURE:
<223> OTHER INFORMATION: synthetic construct

<400> SEQUENCE: 2

```
atggctgaca tcaccgacaa gactgccgaa caattggaaa acttgaacat tcaagacgat     60
cagaagcaag ctgccactgg ttccgaatct caatccgtcg aaaactcttc cgcttctttg    120
tacgttggtg acttagaacc atctgtctcc gaagctcact tgtacgacat cttctctcca    180
atcggttccg tctcttccat cagagtttgt cgtgatgcta tcaccaagac cagcttgggt    240
tacgcttacg tcaactttaa cgaccatgaa gctggcagaa aggctatcga acaattgaac    300
tacactccaa tcaagggtag actatgtaga atcatgtggt ctcaacgtga tccatccttg    360
agaaagaaag gttctggcaa catcttcatc aagaacttgc atccagacat tgacaacaag    420
gctttgtacg atactttcag tgtctttggt gacatcttat cttccaagat tgctaccgac    480
gaaaacggaa agtccaaggg ttttggcttt gttcacttcg aagaggaagg tgctgccaag    540
gaagctatcg atgctttgaa tggtatgcta ttgaacggtc aagaaatcta cgttgctcct    600
cacttgtcca gaaggaacg tgactctcaa ttggaagaga ccaaggctca ctacaccaac    660
ttgtacgtca agaatatcaa ctccgaaact accgacgaac aatttcaaga attgtttgcc    720
aagtttggtc caattgtttc tgcttccttg gaaaaggatg ccgacggcaa gttgaagggt    780
ttcggtttcg tcaactacga aaagcacgaa gacgctgtca aggctgtcga agccttgaac    840
gattccgaac taaatggcga aaagttgtac gttggtagag cacagaaaaa gaacgaacgt    900
atgcacgtct tgaagaaaca atacgaagct tacagattgg aaaagatggc caagtaccaa    960
ggtgttaatt tgttcgtcaa gaacttggac gattctgtcg atgacgaaaa gttggaagag   1020
gaatttgctc catacggtac tatcacctct gccaaggtca tgagaaccga aaacggtaag   1080
tccaagggtt ttggcttcgt ctgtttctct actccagagg aagctaccaa ggctatcacc   1140
gaaaagaatc aacagattgt tgctggcaag ccattgtacg ttgccattgc tcaaagaaag   1200
gacgtcagac gttctcaact agctcaacag atccaagcca gaaaccaaat gagataccaa   1260
caggctactg ctgccgctgc agctgccgct gcaggtatgc caggtcaatt catgcctcca   1320
atgttttacg tgtcatgcc tccaagaggt gttccattca acggtccaaa ccctcaacag   1380
atgaatccaa tgggtggaat gccaaagaac ggtatgcctc cacaattcag aaacggtcca   1440
gtctacggtg tccctccaca aggtggcttt ccaagaaacg ctaacgacaa caatcaattc   1500
taccaacaga agcaaagaca agctttgggt gaacaattgt acaagaaagt ttctgccaag   1560
acttccaacg aagaagctgc aggcaagatc actggtatga tcttggattt accacctcaa   1620
gaagtcttcc cactattgga atccgacgaa ttgttcgaac aacactacaa ggaggcttct   1680
gctgcctacg aatctttcaa aaaggaacaa gagcaacaga ctgaacaagc ctaa         1734
```

<210> SEQ ID NO 3
<211> LENGTH: 780
<212> TYPE: DNA
<213> ORGANISM: Artificial Sequence
<220> FEATURE:
<223> OTHER INFORMATION: synthetic construct

<400> SEQUENCE: 3

```
tatgttgtac ctaaatcaat accgacagct tttgacatat tatctgttat ttacttgaat     60
ttttgtttct tgtaatactt gattactttt cttttgatgt gcttatctta caaatagaga    120
aaataaaaca acttaagtaa gaattgggaa acgaaactac aactcaatcc cttctcgaag    180
atacatcaat ccaccccctta tataaccttg aagtcctcga acgatcagc taatctaaat    240
```

```
ggccccccctt  cttttttgggt  tctttctctc  cctcttgccg  ccgatggaac  gttctggaaa      300
aagaagaata   atttaattac   tttctcaact  aaaatctgga  gaaaaaacgc  aaatgacagc      360
ttctaaacgt   tccgtgtgct   ttctttctag  aatgttctgg  aaagtttaca  acaatccaca      420
agaacgaaaa   tgccgttgac   aatgatgaaa  ccatcatcca  cacaccgcgc  acacgtgctt      480
tatttctttt   tctgaattt    tttttccgc   cattttcaac  caaggaaatt  ttttttctta     540
gggctcagaa   cctgcaggtg   aagaagcgct  ttagaaatca  aagcacaacg  caacaatttg      600
tcgacaaccg   agcctttgaa   gaaaaaattt  ttcacattgt  cgcctctaaa  taaatagttt      660
aaggttatct   acccactata   tttagttggt  tctttttttt  ttccttctac  tctttatctt      720
tttacctcat   gctttctacc   tttcagcact  gaagagtcca  accgaatata  tacacacata      780
```

<210> SEQ ID NO 4
<211> LENGTH: 389
<212> TYPE: DNA
<213> ORGANISM: Artificial Sequence
<220> FEATURE:
<223> OTHER INFORMATION: synthetic construct

<400> SEQUENCE: 4

```
attaatataa   ttatataaaa   atattatctt  cttttcttta  tatctagtgt  tatgtaaaat       60
aaattgatga   ctacggaaag   cttttttata  ttgtttcttt  ttcattctga  gccacttaaa      120
tttcgtgaat   gttcttgtaa   gggacggtag  atttacaagt  gatacaacaa  aaagcaaggc      180
gcttttctca   ataaaaagaa   gaaaagcatt  taacaattga  acacctctat  atcaacgaag      240
aatattactt   tgtctctaaa   tccttgtaaa  atgtgtacga  tctctatatg  ggttactcat      300
aagtgtaccg   aagactgcat   tgaaagttta  tgttttttca  ctggaggcgt  cattttcgcg      360
ttgagaagat   gttcttatcc   aaatttcaa                                           389
```

REDUCTION IN ACETATE PRODUCTION BY YEAST OVER-EXPRESSING PAB1

TECHNICAL FIELD

The present compositions and methods relate to modified yeast that over-expresses polyadenylate-binding protein (PAB1). The yeast produces a deceased amount of acetate compared to their parental cells. Such yeast is particularly useful for large-scale ethanol production from starch substrates, where acetate in an undesirable by-product.

BACKGROUND

First-generation yeast-based ethanol production converts sugars into fuel ethanol. The annual fuel ethanol production by yeast is about 90 billion liters worldwide (Gombert, A. K. and van Maris. A. J. (2015) *Curr. Opin. Biotechnol.* 33:81-86). It is estimated that about 70% of the cost of ethanol production is the feedstock. Since the production volume is so large, even small yield improvements have massive economic impact across the industry.

The phosphoketolase (PKL) pathway has been genetically engineered into yeast to increase ethanol production, as described in WO2015148272 (Miasnikov et al.). Unfortunately, the engineered strains also produce more acetate than the parental yeast. Acetate is not a desirable by-product as it has negative effects on yeast growth and fermentation. In addition, acetate reduces the pH of left-over water from fermentation and distillation, referred to as backset, which is typically reused for liquefaction of a subsequent batch of substrate. As a result, ethanol producers must adjust the pH of the backset (or liquefact) or increase the amount of fresh water used for liquefaction.

The need exists to control the amount of acetate produced by yeast, particularly engineered yeast that tend to produce an increased amount of acetate.

SUMMARY

The present compositions and methods relate to modified yeast that over-express the PAB1 polypeptide. Aspects and embodiments of the compositions and methods are described in the following, independently-numbered, paragraphs.

1. In one aspect, modified yeast cells derived from parental yeast cells are provided, the modified cells comprising a genetic alteration that causes the modified cells to produce an increased amount of PAB1 polypeptides compared to the parental cells, wherein the modified cells produce during fermentation a decreased amount of acetate compared to the amount of acetate produced by the parental cells under identical fermentation conditions.

2. In some embodiments of the modified cells of paragraph 1, the genetic alteration comprises the introduction into the parental cells of a nucleic acid capable of directing the expression of a PAB1 polypeptide to a level above that of the parental cell grown under equivalent conditions.

3. In some embodiments of the modified cells of paragraph 1, the genetic alteration comprises the introduction of an expression cassette for expressing a PAB1 polypeptide.

4. In some embodiments of the modified cells of any of paragraphs 1-3, the cells further comprising one or more genes of the phosphoketolase pathway.

5. In some embodiments of the modified cells of paragraph 4, the genes of the phosphoketolase pathway are selected from the group consisting of phosphoketolase, phosphotransacetylase and acetylating acetyl dehydrogenase.

6. In some embodiments of the modified cells of any of paragraphs 1-5, the amount of increase in the expression of the PAB1 polypeptide is at least about 200% compared to the level expression in the parental cells grown under equivalent conditions.

7. In some embodiments of the modified cells of any of paragraphs 1-5, the amount of increase in the production of mRNA encoding the PAB1 polypeptide is at least about 400% compared to the level in the parental cells grown under equivalent conditions.

8. In some embodiments of the modified cells of any of paragraphs 1-7, the cells further comprise an exogenous gene encoding a carbohydrate processing enzyme.

9. In some embodiments, the modified cells of any of paragraphs 1-8, further comprise an alteration in the glycerol pathway and/or the acetyl-CoA pathway.

10. In some embodiments, the modified cells of any of paragraphs 1-9, further comprise an alternative pathway for making ethanol.

11. In some embodiments of the modified cells of any of paragraphs 1-10, the cells are of a *Saccharomyces* spp.

12. In another aspect, a method for decreasing the production of acetate from yeast cells grown on a carbohydrate substrate is provided, comprising: introducing into parental yeast cells a genetic alteration that increases the production of PAB1 polypeptides compared to the amount produced in the parental cells.

13. In some embodiments of the method of paragraph 12, the cells having the introduced genetic alteration are the modified cells are the cells of any of paragraphs 1-11.

14. In some embodiments of the method of paragraph 12 or 13, the decrease in acetate production is at least 10%, at least 15%, at least 20%, or at least 25%.

15. In some embodiments of the method of any of paragraphs 12-14, PAB1 polypeptides are over-expressed by at least 200%.

16. In some embodiments of the method of any of paragraphs 12-14, PAB1 polypeptides are over-expressed by at least 15-fold.

These and other aspects and embodiments of present modified cells and methods will be apparent from the description, including any accompanying Drawings/Figures.

DETAILED DESCRIPTION

I. Definitions

Prior to describing the present yeast and methods in detail, the following terms are defined for clarity. Terms not defined should be accorded their ordinary meanings as used in the relevant art.

As used herein, the term "alcohol" refers to an organic compound in which a hydroxyl functional group (—OH) is bound to a saturated carbon atom.

As used herein, the terms "yeast cells," "yeast strains," or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "engineered yeast cells," "variant yeast cells," "modified yeast cells," or similar phrases, refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins," or "homologs." Such proteins can be derived from organisms of different genera and/or species, or different classes of organisms (e.g., bacteria and fungi), or artificially designed. Related proteins also encompass homologs determined by primary sequence analysis, determined by secondary or tertiary structure analysis, or determined by immunological cross-reactivity, or determined by their functions.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme (s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'S, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF |

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype. The term "allele" is generally preferred when an organism contains more than one similar genes, in which case each different similar gene is referred to as a distinct "allele."

As used herein, "constitutive" expression refers to the production of a polypeptide encoded by a particular gene under essentially all typical growth conditions, as opposed to "conditional" expression, which requires the presence of a particular substrate, temperature, or the like to induce or activate expression.

As used herein, the term "expressing a polypeptide" and similar terms refers to the cellular process of producing a polypeptide using the translation machinery (e.g., ribosomes) of the cell.

As used herein, "over-expressing a polypeptide," "increasing the expression of a polypeptide," and similar terms, refer to expressing a polypeptide at higher-than-normal levels compared to those observed with parental or "wild-type cells that do not include a specified genetic modification.

As used herein, an "expression cassette" refers to a DNA fragment that includes a promoter, and amino acid coding region and a terminator (i.e., promoter::amino acid coding region::terminator) and other nucleic acid sequence needed to allow the encoded polypeptide to be produced in a cell. Expression cassettes can be exogenous (i.e., introduced into a cell) or endogenous (i.e., extant in a cell).

As used herein, the terms "fused" and "fusion" with respect to two DNA fragments, such as a promoter and the coding region of a polypeptide refer to a physical linkage causing the two DNA fragments to become a single molecule.

As used herein, the terms "wild-type" and "native" are used interchangeably and refer to genes, proteins or strains found in nature, or that are not intentionally modified for the advantage of the presently described yeast.

As used herein, the term "protein of interest" refers to a polypeptide that is desired to be expressed in modified yeast. Such a protein can be an enzyme, a substrate-binding protein, a surface-active protein, a structural protein, a selectable marker, a signal transducer, a receptor, a transporter, a transcription factor, a translation factor, a co-factor, or the like, and can be expressed. The protein of interest is encoded by an endogenous gene or a heterologous gene (i.e., gene of interest") relative to the parental strain. The protein of interest can be expressed intracellularly or as a secreted protein.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using CRISPR, RNAi, antisense, or any other method that abolishes gene expression. A gene can be disrupted by deletion or genetic manipulation of non-adjacent control elements. As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements. Deletion of a gene also refers to the deletion a part of the coding sequence, or a part of promoter immediately or not immediately adjacent to the coding sequence, where there is no functional activity of the interested gene existed in the engineered cell.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "functional polypeptide/protein" is a protein that possesses an activity, such as an enzymatic activity, a binding activity, a surface-active property, a signal transducer, a receptor, a transporter, a transcription factor, a translation factor, a co-factor, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway," i.e., a biochemical pathway, refers broadly to any genetic or chemical manipulation that reduces or completely stops the flux of biochemical substrates or intermediates through a metabolic pathway. Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth in the presence of oxygen.

As used herein, "anaerobic fermentation" refers to growth in the absence of oxygen.

As used herein, the expression "end of fermentation" refers to the stage of fermentation when the economic advantage of continuing fermentation to produce a small amount of additional alcohol is exceeded by the cost of continuing fermentation in terms of fixed and variable costs. In a more general sense, "end of fermentation" refers to the point where a fermentation will no longer produce a significant amount of additional alcohol, i.e., no more than about 1% additional alcohol, or no more substrate left for further alcohol production.

As used herein, the expression "carbon flux" refers to the rate of turnover of carbon molecules through a metabolic pathway. Carbon flux is regulated by enzymes involved in metabolic pathways, such as the pathway for glucose metabolism and the pathway for maltose metabolism.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

EC enzyme commission
PKL phosphoketolase
PTA phosphotransacetylase
AADH acetaldehyde dehydrogenases
ADH alcohol dehydrogenase
EtOH ethanol
AA α-amylase
GA glucoamylase
° C. degrees Centigrade
bp base pairs
DNA deoxyribonucleic acid
ds or DS dry solids
g or gm gram
g/L grams per liter
$H_2O$ water
HPLC high performance liquid chromatography
hr or h hour
kg kilogram
M molar
mg milligram
mL or ml milliliter
min minute
mM millimolar
N normal
nm nanometer
PAB1 polyadenylate-binding protein
PCR polymerase chain reaction
ppm parts per million
Δ relating to a deletion
microgram
μL and μl microliter
μM micromolar

II. Modified Yeast Cells Having Increased PAB1 Expression

Described are modified yeast and methods having a genetic alteration that results in the production of increased amounts of PAB1 polypeptides compared to corresponding (i.e., otherwise-identical) parental cells. PAB1 is the major poly(A)-binding protein in yeast. It is an approximately 577-amino acid residue, multifunctional-protein that mediates many cellular functions associated with the 3'-poly(A)-tail of messenger RNAs (see, e.g., Brune, C. et al. (2005) RNA. 11:517-531). Over-expression of PAB1 increased stress tolerance of engineered yeast (Martani, F. et al., (2015), Sci. Rep. 5: 18318; doi: 10.1038/srep18318). No association has heretofore been made between PAB1 expression and acetate reduction in engineered yeast.

Applicants have discovered that yeast cells over-expressing PAB1 polypeptides produce a decreased amount of acetate compared to otherwise-identical parental cells. Decreased acetate is desirable as acetate adversely affects yeast growth and fermentation and additionally results in backset that has a lower than desirable pH, requiring pH adjustment or the use of more fresh water to dilute the backset.

In some embodiments, the increase in the amount of PAB1 polypeptides produced by the modified cells is an increase of at least 20%, at least 30%, at least 40%, at least 50%, at least 70%, at least 100%, at least 150%, at least 200%, at least 500%, at least 1000%, or more, especially at later stage of fermentation, compared to the amount of PAB1 polypeptides produced by parental cells grown under the same conditions.

In some embodiments, the increase in the amount of PAB1 polypeptides produced by the modified cells is at least 2-fold, at least 5-fold, at least 10-fold, at least 20-fold, at least 30-fold or more, compared to the amount of PAB1 polypeptides produced by parental cells grown under the same conditions.

In some embodiments, the increase in the strength of the promoter used to control expression of the PAB1 polypeptides produced by the modified cells is at least 2-fold, at least 5-fold, at least 10-fold, at least 13-fold, at least 20-fold, at least 30-fold, or more, compared to strength of the native promoter controlling PAB1 expression, based on the amount of mRNA produced. RNAseq data (see, e.g., Wang, Z. et al. (2009) Nature Rev. Gen. 10:57-63) indicates that the EFB1 promoter used for the exemplified PAB1 expression cassette is approximately 13-times stronger than the normal PAB1 promoter.

In some embodiments, the decrease in acetate production by the modified cells is a decrease of at least 10%, at least 15%, at least 20%, at least 25%, at least 30%, at least 35%, at least 40%, or at least 50%, more, compared to the amount of acetate produced by parental cells grown under the same conditions.

Preferably, increased PAB1 expression is achieved by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the present compositions and methods involve introducing into yeast cells a nucleic acid capable of directing the over-expression, or increased expression, of a PAB1 polypeptide. Particular methods include but are not limited to (i) introducing an exogenous expression cassette for producing the polypeptide into a host cell, optionally in addition to an endogenous expression cassette, (ii) substituting an exogenous expression cassette with an endogenous cassette that allows the production of an increased amount of the polypeptide, (iii) modifying the promoter of an endogenous expression cassette to increase expression, (iv) increase copy number of the same or different cassettes for over-expression of PAB1, and/or (v) modifying any aspect of the host cell to increase the half-life of the polypeptide in the host cell.

In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

In some embodiments, the parental cell that is modified already includes an engineered pathway of interest, such as a PKL pathway to increases ethanol production, or any other pathway to increase alcohol production.

The amino acid sequence of the exemplified S. cerevisiae PAB1 polypeptide is shown, below, as SEQ ID NO: 1:

MADITDKTAEQLENLNIQDDQKQAATGSESQSVENSSASLYVGDLEPSV

SEAHLYDIFSPIGSVSSIRVCRDAITKTSLGYAYVNFNDHEAGRKAIEQ

LNYTPIKGRLCRIMWSQRDPSLRKKGSGNIFIKNLHPDIDNKALYDTFS

```
-continued
VFGDILSSKIATDENGKSKGFGFVHFEEEGAAKEAIDALNGMLLNGQEI

YVAPHLSRKERDSQLEETKAHYTNLYVKNINSETTDEQFQELFAKFGPI

VSASLEKDADGKLKGFGFVNYEKHEDAVKAVEALNDSELNGEKLYVGRA

QKKNERMHVLKKQYEAYRLEKMAKYQGVNLFVKNLDDSVDDEKLEEEFA

PYGTITSAKVMRTENGKSKGFGFVCFSTPEEATKAITEKNQQIVAGKPL

YVAIAQRKDVRRSQLAQQIQARNQMRYQQATAAAAAAAAGMPGQFMPPM

FYGVMPPRGVPFNGPNPQQMNPMGGMPKNGMPPQFRNGPVYGVPPQGGF

PRNANDNNQFYQQKQRQALGEQLYKKVSAKTSNEEAAGKITGMILDLPP

QEVFPLLESDELFEQHYKEASAAYESFKKEQEQQTEQA
```

The NCBI database includes over 100 entries for *S. cerevisiae* PAB1 polypeptides. Natural variations in the amino acid sequence are not expected to affect its function. In addition, based on such BLAST and Clustal W data, it is apparent that the exemplified *S. cerevisiae* PAB1 polypeptide shares a high degree of sequence identity to polypeptides from other organisms, and over-expression of functionally and/or structurally similar proteins, homologous proteins and/or substantially similar or identical proteins, is expected to produce similar beneficial results.

In particular embodiments of the present compositions and methods, the amino acid sequence of the PAB1 polypeptide that is over-expressed in modified yeast cells has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

III. Modified Yeast Cells Having Increased PAB1 Expression in Combination with Genes of an Exogenous PKL Pathway Increased expression of PAB1 can be combined with expression of genes in the PKL pathway to reduce the production of elevated amounts of acetate that is associated with introducing an exogenous PKL pathway into yeast.

Engineered yeast cells having a heterologous PKL pathway have been previously described in WO2015148272 (Miasnikov et al.). These cells express heterologous phosphoketolase (PKL), phosphotransacetylase (PTA) and acetylating acetyl dehydrogenase (AADH), optionally with other enzymes, to channel carbon flux away from the glycerol pathway and toward the synthesis of acetyl-CoA, which is then converted to ethanol. Such modified cells are capable of increased ethanol production in a fermentation process when compared to otherwise-identical parent yeast cells.

IV. Combination of Increased Active PAB1 Production with Other Mutations that Affect Alcohol Production In some embodiments, in addition to expressing increased amounts of active PAB1 polypeptides, optionally in combination with introducing an exogenous PKL pathway, the present modified yeast cells include additional modifications that affect ethanol production.

The modified cells may further include mutations that result in attenuation of the native glycerol biosynthesis pathway and/or reuse glycerol pathway, which are known to increase alcohol production. Methods for attenuation of the glycerol biosynthesis pathway in yeast are known and include reduction or elimination of endogenous NAD-dependent glycerol glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.). Methods to enhance the reuse glycerol pathway by over expression of glycerol dehydrogenase (GCY1) and dihydroxyacetone kinase (DAK1) to convert glycerol to dihydroxyacetone phosphate (Zhang et al; *J Ind Microbiol Biotechnol* (2013) 40:1153-1160).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This partially reduces the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like.

In some embodiments the modified cells may further include a heterologous gene encoding a protein with $NAD^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.). In some embodiments of the present compositions and methods the yeast expressly lacks a heterologous gene(s) encoding an acetylating acetaldehyde dehydrogenase, a pyruvate-formate lyase or both.

In some embodiments, the present modified yeast cells may further over-express a sugar transporter-like (STL1) polypeptide to increase the uptake of glycerol (see, e.g., Ferreira et al., 2005; Dušková et al., 2015 and WO 2015023989 A1).

In some embodiments, the present modified yeast cells further include a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

V. Combination of Increased Expression PAB1 with Other Beneficial Mutations

In some embodiments, in addition to increased expression of PAB1 polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in the increased production of active HAC1 polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Use of the Modified Yeast for Increased Alcohol Production

The present compositions and methods include methods for increasing alcohol production and/or reducing glycerol production, in fermentation reactions. Such methods are not limited to a particular fermentation process. The present engineered yeast is expected to be a "drop-in" replacement for convention yeast in any alcohol fermentation facility. While primarily intended for fuel alcohol production, the present yeast can also be used for the production of potable alcohol, including wine and beer.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present yeast strains and methods will be apparent to the skilled person in view of the present description. The following examples are intended to further illustrate, but not limit, the compositions and methods.

EXAMPLES

Example 1

Materials and Methods

Liquefact Preparation:
Liquefact (corn mash slurry) was prepared by adding 600 ppm of urea, 0.124 SAPU/g ds FERMGEN™ 2.5× (acid fungal protease), 0.33 GAU/g ds CS4 (a variant *Trichoderma* glucoamylase) and 1.46 SSCU/g ds AKAA (*Aspergillus kawachii* α-amylase), adjusted to a pH of 4.8.

Serum Vial Assays:
2 mL of YPD in 24-well plates were inoculated with yeast cells and the cultures allowed to grow overnight to an OD between 25-30. 5 mL liquefact (5.6 g) was transferred to serum vials (Chemglass, Catalog No. CG-4904-01) and yeast was added to each vial to a final OD of about 0.3. The lids of the vials were installed and punctured with needle (BD, Catalog No. 305111) for ventilation (to release $CO_2$), then incubated at 32° C. with shaking at 200 RPM for 55 hours.

AnKom Assays:
300 μL of concentrated yeast overnight culture was added to each of a number ANKOM bottles filled with 50 g prepared liquefact (see above) to a final OD of 0.3. The bottles were then incubated at 32° C. with shaking at 150 RPM for 55 hours.

HPLC Analysis:
Samples of the cultures from serum vials and AnKom assays were collected in Eppendorf tubes by centrifugation for 12 minutes at 14,000 RPM. The supernatants were filtered using 0.2 μM PTFE filters and then used for HPLC (Agilent Technologies 1200 series) analysis with the following conditions: Bio-Rad Aminex HPX-87H columns, running temperature of 55 C. 0.6 ml/min isocratic flow 0.01 N $H_2SO_4$, 2.5 μl injection volume. Calibration standards were used for quantification of the of acetate, ethanol, glycerol, glucose and other molecules. All values are reported in g/L.

Example 2

Preparation of a PAB1 Expression Cassette

The PAB1 gene of *Saccharomyces cerevisiae* was codon optimized and synthesized to generate the artificial gene, "PAB1s." The EFB1 promoter (YAL003W locus; SEQ ID NO: 3) and TPI terminator (YDR050C locus; SEQ ID NO: 4) were operably linked to the coding sequence to generate EFB1Pro::PAB1s::Tpi1Ter expression cassette. This expression cassette was introduced at the upstream region of the AAP1 locus (YHR047C) of either (i) FERMAX™ Gold (Martrex Inc., Minnesota, USA; herein abbreviated, "FG"), a well-known fermentation yeast used in the grain ethanol industry, or (ii) FG-PKR, engineered FG yeast having a heterologous phosphoketolase (PKL) pathway involving the expression of phosphoketolase (PKL), phosphotransacetylase (PTA) and acetylating acetyl dehydrogenase (AADH) as described in WO2015148272 (Miasnikov et al.) using CRISPR Cas9 technology. The expected insertion of the PAB1 expression cassette in the two parental strains was confirmed by PCR.

```
The amino acid sequence of the PAB1 polypeptide
is shown, below, as SEQ ID NO: 1:
MADITDKTAEQLENLNIQDDQKQAATGSESQSVENSSASLYVGDLEPSVS

EAHLYDIFSPIGSVSSIRVCRDAITKTSLGYAYVNFNDHEAGRKAIEQLN

YTPIKGRLCRIMWSQRDPSLRKKGSGNIFIKNLHPDIDNKALYDTFSVFG

DILSSKIATDENGKSKGFGFVHFEEEGAAKEAIDALNGMLLNGQEIYVAP

HLSRKERDSQLEETKAHYTNLYVKNINSETTDEQFQELFAKFGPIVSASL

EKDADGKLKGFGFVNYEKHEDAVKAVEALNDSELNGEKLYVGRAQKKNER

MHVLKKQYEAYRLEKMAKYQGVNLFVKNLDDSVDDEKLEEEFAPYGTITS

AKVMRTENGKSKGFGFVCFSTPEEATKAITEKNQQIVAGKPLYVAIAQRK

DVRRSQLAQQIQARNQMRYQQATAAAAAAAAGMPGQFMPPMFYGVMPPRG

VPFNGPNPQQMNPMGGMPKNGMPPQFRNGPVYGVPPQGGFPRNANDNNQF

YQQKQRQALGEQLYKKVSAKTSNEEAAGKITGMILDLPPQEVFPLLESDE

LFEQHYKEASAAYESFKKEQEQQTEQA

The PAB1-coding region of the PAB1s gene is shown,
below, as SEQ ID NO: 2:
ATGGCTGACATCACCGACAAGACTGCCGAACAATTGGAAAACTTGAACAT

TCAAGACGATCAGAAGCAAGCTGCCACTGGTTCCGAATCTCAATCCGTCG

AAAACTCTTCCGCTTCTTTGTACGTTGGTGACTTAGAACCATCTGTCTCC

GAAGCTCACTTGTACGACATCTTCTCTCCAATCGGTTCCGTCTCTTCCAT

CAGAGTTTGTCGTGATGCTATCACCAAGACCAGCTTGGGTTACGCTTACG

TCAACTTTAACGACCATGAAGCTGGCAGAAAGGCTATCGAACAATTGAAC

TACACTCCAATCAAGGGTAGACTATGTAGAATCATGTGGTCTCAACGTGA

TCCATCCTTGAGAAAGAAAGGTTCTGGCAACATCTTCATCAAGAACTTGC

ATCCAGACATTGACAACAAGGCTTTGTACGATACTTTCAGTGTCTTTGGT

GACATCTTATCTTCCAAGATTGCTACCGACGAAAACGGAAAGTCCAAGGG

TTTTGGCTTTGTTCACTTCGAAGAGGAAGGTGCTGCCAAGGAAGCTATCG

ATGCTTTGAATGGTATGCTATTGAACGGTCAAGAAATCTACGTTGCTCCT

CACTTGTCCAGAAAGGAACGTGACTCTCAATTGGAAGAGACCAAGGCTCA

CTACACCAACTTGTACGTCAAGAATATCAACTCCGAAACTACCGACGAAC

AATTTCAAGAATTGTTTGCCAAGTTTGGTCCAATTGTTTCTGCTTCCTTG

GAAAAGGATGCCGACGGCAAGTTGAAGGGTTTCGGTTTCGTCAACTACGA

AAAGCACGAAGACGCTGTCAAGGCTGTCGAAGCCTTGAACGATTCCGAAC

TAAATGGCGAAAAGTTGTACGTTGGTAGAGCACAGAAAAAGAACGAACGT

ATGCACGTCTTGAAGAAACAATACGAAGCTTACAGATTGGAAAAGATGGC

CAAGTACCAAGGTGTTAATTTGTTCGTCAAGAACTTGGACGATTCTGTCG

ATGACGAAAAGTTGGAAGAGGAATTTGCTCCATACGGTACTATCACCTCT

GCCAAGGTCATGAGAACCGAAAACGGTAAGTCCAAGGGTTTTGGCTTCGT

CTGTTTCTCTACTCCAGAGGAAGCTACCAAGGCTATCACCGAAAAGAATC

AACAGATTGTTGCTGGCAAGCCATTGTACGTTGCCATTGCTCAAAGAAAG

GACGTCAGACGTTCTCAACTAGCTCAACAGATCCAAGCCAGAAACCAAAT

GAGATACCAACAGGCTACTGCTGCCGCTGCAGCTGCCGCTGCAGGTATGC

CAGGTCAATTCATGCCTCCAATGTTTTACGGTGTCATGCCTCCAAGAGGT

GTTCCATTCAACGGTCCAAACCCTCAACAGATGAATCCAATGGGTGGAAT

GCCAAAGAACGGTATGCCTCCACAATTCAGAAACGGTCCAGTCTACGGTG

TCCCTCCACAAGGTGGCTTTCCAAGAAACGCTAACGACAACAATCAATTC

TACCAACGAAGCAAAGACAAGCTTTGGGTGAACAATTGTACAAGAAAGT

TTCTGCCAAGACTTCCAACGAAGAAGCTGCAGGCAAGATCACTGGTATGA

TCTTGGATTTACCACCTCAAGAAGTCTTCCCACTATTGGAATCCGACGAA

TTGTTCGAACAACACTACAAGGAGGCTTCTGCTGCCTACGAATCTTTCAA

AAAGGAACAAGAGCAACAGACTGAACAAGCCTAA

The EFB1 promoter region used for PAB1s over-
expression shown, below, as SEQ ID NO: 3:
TATGTTGTACCTAAATCAATACCGACAGCTTTTGACATATTATCTGTTAT

TTACTTGAATTTTTGTTTCTTGTAATACTTGATTACTTTTCTTTTGATGT

GCTTATCTTACAAATAGAGAAAATAAAACAACTTAAGTAAGAATTGGGAA

ACGAAACTACAACTCAATCCCTTCTCGAAGATACATCAATCCACCCCTTA

TATAACCTTGAAGTCCTCGAAACGATCAGCTAATCTAAATGGCCCCCCTT

CTTTTTGGGTTCTTTCTCTCCCTCTTGCCGCCGATGGAACGTTCTGGAAA

AAGAAGAATAATTTAATTACTTTCTCAACTAAAATCTGGAGAAAAAACGC

AAATGACAGCTTCTAAACGTTCCGTGTGCTTTCTTTCTAGAATGTTCTGG

AAAGTTTACAACAATCCACAAGAACGAAAATGCCGTTGACAATGATGAAA

CCATCATCCACACACCGCGCACACGTGCTTTATTTCTTTTTCTGAATTTT

TTTTTTCCGCCATTTTCAACCAAGGAAATTTTTTTTCTTAGGGCTCAGAA

CCTGCAGGTGAAGAAGCGCTTTAGAAATCAAAGCACAACGCAACAATTTG

TCGACAACCGAGCCTTTGAAGAAAAAATTTTTCACATTGTCGCCTCTAAA

TAAATAGTTTAAGGTTATCTACCCACTATATTTAGTTGGTTCTTTTTTTT

TTCCTTCTACTCTTTATCTTTTTACCTCATGCTTTCTACCTTTCAGCACT

GAAGAGTCCAACCGAATATATACACACATA

The Tpi1 terminator region used for PAB1s over-
expression shown, below, as SEQ ID NO: 4:
ATTAATATAATTATATAAAAATATTATCTTCTTTTCTTTATATCTAGTGT

TATGTAAAATAAATTGATGACTACGGAAAGCTTTTTTATATTGTTTCTTT

TTCATTCTGAGCCACTTAAATTTCGTGAATGTTCTTGTAAGGGACGGTAG

ATTTACAAGTGATACAACAAAAAGCAAGGCGCTTTTTCTAATAAAAAGAA

GAAAAGCATTTAACAATTGAACACCTCTATATCAACGAAGAATATTACTT

TGTCTCTAAATCCTTGTAAAATGTGTACGATCTCTATATGGGTTACTCAT

AAGTGTACCGAAGACTGCATTGAAAGTTTATGTTTTTTCACTGGAGGCGT

CATTTTCGCGTTGAGAAGATGTTCTTATCCAAATTTCAA
```

Example 3

Alcohol Production Using Yeast that Over-Express PAB1

Strains over-expressing PAB1 were tested in a small vial assay, containing 5.6 g liquefact, and then in an Ankom assay, containing 50 g liquefact, as described in Example 1. Fermentations were performed at 32° C. for 55 hours. Samples from the end of fermentation were analyzed by HPLC. The results are summarized in Tables 1 and 2.

TABLE 1

HPLC results from a small vial assays

| Strain features | Glycerol (g/L) | Acetate (g/L) | Glucose (g/L) | Ethanol (g/L) | Acetate reduction (%) |
|---|---|---|---|---|---|
| FG | 13.767 | 1.275 | 0.291 | 143.839 | -0- |
| FG-PAB1 | 14.707 | 1.063 | 0.173 | 143.039 | 16.6% |
| FG-PKL | 12.811 | 1.744 | 0.583 | 145.101 | -0- |
| FG-PKL-PAB1 | 13.554 | 1.308 | 0.661 | 144.524 | 25.0% |

TABLE 2

HPLC results from an Ankom assay

| Strain features | Glucose (g/L) | Glycerol (g/L) | Acetate (g/L) | Ethanol g/L | Acetate reduction (%) |
|---|---|---|---|---|---|
| FG | 0.32 | 13.15 | 0.90 | 140.20 | -0- |
| FG-PAB1 | 0.31 | 13.91 | 0.79 | 140.11 | 12.2% |
| FG-PKL | 0.61 | 11.94 | 1.42 | 141.45 | -0- |
| FG-PKL-PAB1 | 0.71 | 12.69 | 1.06 | 140.33 | 25.4% |

Over-expression of PAB1 resulted in a decrease in acetate production of about 12-17% in FG yeast, which is recognized as a robust, high-ethanol-producing yeast for the fuel ethanol industry, while not being a genetically engineered organism. Over-expression of PAB1 resulted in a decrease of up to almost twice as much in FG yeast engineered to have an exogenous PKL pathway. These results demonstrate that PAB1 over-expression is beneficial for reducing acetate, in general, but is particularly beneficial for reducing the increased amount of acetate produced by yeast having a PKL pathway.

What is claimed is:

1. Modified yeast cells derived from parental yeast cells, the modified cells comprising:
   (a) a genetic alteration that causes the modified cells to produce an increased amount of PAB1 polypeptides compared to the parental cells, wherein the genetic alteration comprises an introduction into the parental cells of a nucleic acid capable of directing the expression of a PAB1 polypeptide to a level above that of the parental cell grown under equivalent conditions; and
   (b) one or more heterologous genes of a phosphoketolase pathway; and
   wherein the modified cells produce during fermentation a decreased amount of acetate compared to the amount of acetate produced by the parental cells under identical fermentation conditions.

2. The modified cells of claim 1, wherein the introduction into the parental cells of a nucleic acid comprises:
   (a) introduction of an exogenous expression cassette for producing the PAB1 polypeptide into the host cell;
   (b) modification of a promoter of an endogenous expression cassette to increase expression of the PAB1 polypeptide; and/or
   (c) increasing the copy number of the same or different cassettes for over-expression of PAB1.

3. The modified cells of claim 1, wherein the genetic alteration comprises the introduction of an expression cassette for expressing a PAB1 polypeptide.

4. The modified cells of claim 1 PE wherein the one or more heterologous genes of the phosphoketolase pathway are selected from the group consisting of phosphoketolase, phosphotransacetylase and acetylating acetyl dehydrogenase.

5. The modified cells of claim 1, wherein the amount of increase in the expression of the PAB1 polypeptide is at least about 200% compared to the level of expression in the parental cells grown under equivalent conditions.

6. The modified cells of claim 1, wherein the amount of increase in the production of mRNA encoding the PAB1 polypeptide is at least about 400% compared to the level in the parental cells grown under equivalent conditions.

7. The modified cells of claim 1, wherein the cells further comprise an exogenous gene encoding a carbohydrate processing enzyme.

8. The modified cells of claim 1, further comprising an alteration in the glycerol pathway and/or the acetyl-CoA pathway.

9. The modified cells of claim 1, further comprising an alternative pathway for making ethanol.

10. The modified cells of any of claims 1, wherein the cells are of a *Saccharomyces* spp.

11. A method for decreasing the production of acetate from yeast cells grown on a carbohydrate substrate, comprising: introducing into parental yeast cells a genetic alteration that increases the production of PAB1 polypeptides compared to the amount produced in the parental cells, wherein the genetic alteration comprises introducing into the parental cells a nucleic acid capable of directing the expression of a PAB1 polypeptide to a level above that of the parental cell grown under equivalent conditions.

12. The method of claim 11, wherein the cells having the introduced genetic alteration are the modified cells of claim 1.

13. The method of claim 11, wherein the decrease in acetate production is at least 10%, at least 15%, at least 20%, or at least 25%.

14. The method of claim 11, wherein PAB1 polypeptides are over-expressed by at least 200%.

15. The method of claim 1, wherein PAB 1 polypeptides are over-expressed by at least 15-fold.

* * * * *